US00PP14384P39

(12) United States Plant Patent
Friday

(10) Patent No.: US PP14,384 P3
(45) Date of Patent: Dec. 16, 2003

(54) PEACH TREE NAMED 'P.F. LUCKY 13'

(50) Latin Name: *Prunus persica*
Varietal Denomination: P.F. Lucky 13

(76) Inventor: Paul Jan Friday, P.O. Box 850, Coloma, MI (US) 49038

( * ) Notice: Subject to any disclaimer, the term of this patent is extended or adjusted under 35 U.S.C. 154(b) by 0 days.

(21) Appl. No.: 10/087,959

(22) Filed: Mar. 5, 2002

(65) Prior Publication Data

US 2003/0172420 P1 Sep. 11, 2003

(51) Int. Cl.[7] ..... A01H 5/00
(52) U.S. Cl. ..... Plt./199
(58) Field of Search ..... Plt./199

*Primary Examiner*—Bruce R. Campell
*Assistant Examiner*—W C Haas

(57) ABSTRACT

A new and distinct variety of peach, *Prunus persica*, tree having the following unique combination of desirable features:

1. Producing a very firm fruit that can best be described as "crunchy" when bitten into when firm ripe.
2. The limbs of the tree naturally grow at wide angles creating a wide-spreading tree.
3. A substantially spherical fruit with yellow flesh having red around the pit.
4. A mid-season peach variety that matures after 'Redhaven' (unpatented) and which hangs on the tree for many days staying extremely firm.
5. A peach variety that has excellent storage and shelf life.

2 Drawing Sheets

Botanical classification: *Prunus persica.*

ORIGIN OF VARIETY

The new peach tree (hereinafter referred to as the 'P.F. Lucky 13' peach tree) was originated by Paul Friday in the experimental orchard, which is maintained for the purposes of breeding peach trees, at Paul Friday Farms Inc., located in Coloma, Mich. Coloma is located in the southwest section of Michigan.

In an ongoing mass selection breeding program, superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for their adaptability to local and regional growing conditions. Seeds resulting from open pollination of the trees in the experimental orchard are regularly planted in mass to produce new populations of seedlings which are cultured and monitored to maturity. Trees with superior attributes are retained for further observation and testing, and contribute seeds to advancing generations of new populations of seedlings.

The tree oftis application, 'P.F. Lucky 13', was a single plant from one such a seedling population, and was based on the numerous superior genetic attributes of this tree which are described in the botanical description to follow. While not comprehensive, the details of the botanical description to follow are believed to be a reasonably complete botanical description of the tree of this disclosure.

ASEXUAL REPRODUCTION OF THE VARIETY

The new and distinct variety of peach tree was asexually propagated by budding as performed in the experimental orchard of Paul Friday Farms Inc., located in Coloma, Mich. The asexual propagation demonstrates that such reproduction of the characteristics of the tree are consistent and are established and transmitted through succeeding propagation.

SUMMARY OF THE VARIETY

The new and distinct variety of peach tree is of semi-dwarf, moderate upright growth and a regular and productive bearer of peaches. A distinct characteristic of the 'P.F. Lucky 13' peach tree is its medium vigor having very stubby new growth with short internodes. The buds are generally 1 inch apart on the new growth. The blossoms bloom in mid-season and are characterized by being contracted or partially spread in a ¾ inch diameter during full bloom. At the same time the petals of the blossoms are of lesser length than the length of petals of the normal showy blossom as exemplified by the 'Loring' (unpatented) peach blossom.

The flesh of the fruit of the present peach tree is firm and is yellow.

The skin is smooth having moderate to little down and is of dark red color over about sixty percent to eighty percent (60% to 80%) of its surface at maturity. The red color overlays yellow. Where the red merges with the yellow, the yellow is mottled with the red to a clear light yellow. At maturity the peach is spherical having an average diameter of about 2¾".

The fruit has a firm flesh and may be described as resilient to the extent that the flesh is yieldable and restorable to its original state when subjected to impact forces which may cause bruising and soft blemishes which lead to rejection by the buyer in the fresh market in peaches of the commercial varieties. The fimness of the fruit facilitates handling and packaging of the peaches without damaging the same for shipment. This results in less spoilage and also increases the shelf life.

The fruit matures in the earlier part of the peach growing season of southwestern Michigan. The fruit as mentioned heretofore is of red color over about sixty percent to eighty percent (60% to 80%) of its surface and has a very attractive appearance.

BRIEF DESCRIPTION OF THE PHOTOGRAPHS

In the accompanying photographic illustrations, the top photograph shows the trunk of a six-year-old tree depicting the medium sizes of trunk and branches. It also shows the naturally occurring wide-angle crotches.

The bottom photograph shows a half-bushel basket of whole peaches. The large size of the fruit is apparent as it takes so few fruit to fill the face of the basket. A single peach has been split on a plane ninety degrees to the suture plane to depict the fruit flesh in cross section, the clear yellow flesh, freestone characteristic, and bright red color around the pit.

The next photograph shows the leaves of the plant, depicting both the upper and lower sides and length of the leaves.

DESCRIPTON OF VARIETY

The detailed botanical description of the foliage and fruit of the new variety of peach tree is based upon observations of the specimens grown at Coloma, Mich. with the color terminology, other than the terminology expressed in common terms, in accordance with the Pantone Matching System (PMS) as used internationally to identify printed colors.

Botanical classification: *Prunus persica* cultivar 'P.F. Lucky 13'.

Tree:
- *Age.*—Six (6) years.
- *Height.*—Unpruned 12'.
- *Width.*—Unpruned 10'.
- *Size.*—Medium.
- *Vigor.*—Medium.
- *Density.*—Medium.
- *Form.*—Spreading with naturally formed wide-angle crotches.
- *Production.*—Productive — approximately two-thirds of the fruit must be removed annually to produce good size.
- *Bearer.*—Consistent.
- *Disease resistance to bacterial leaf and fruit spot.*—Very good.

Trunk:
- *Bark.*—Gray (422).
- *Size.*—Medium.
- *Surface.*—Smooth.
- *Diameter.*—4⅜"–24" above the ground at 6 years of age.

Branches:
- *Size.*—Medium to thin — 1⅞" to 2⅝" at trunk union.
- *Surface.*—Medium.
- *Lenticles per square inch on branch.*—Seven (7).
- *Lenticel color.*—407.
- *Crotch angles.*—Strong right angles — almost 90 degrees.
- *Branch color.*—Gray (437).

Leaves:
- *Size.*—Average length 6"— average width 1⅞".
- *Form.*—Lanceolate — pointed.
- *Thickness.*—Medium.
- *Texture.*—Shiny.
- *Margin.*—Finely serrated.
- *Petiole.*—Length 5/16", very short — medium thickness.
- *Gland.*—Varies from 1 to 5 — usually 2 — one on either side of base of leaf or upper portion of petiole.
- *Gland color.*—Yellow.
- *Gland shape.*—Oval.
- *Color.*—Upper surface green (349) — lower surface dull green (349).

Flower buds:
- *Size.*—¾" long, ⅜" wide.
- *Shape.*—Ovoid.
- *Color.*—230.

Flowers:
- *Blooming period.*—May 3, 2001 to May 6, 2001.
- *Size of petals.*—¾" long, ¼" wide.
- *Shape of petals.*—Slightly cupped.
- *Sepal size.*—3/16" long ⅛" wide.
- *Sepal shape.*—Slightly cupped.
- *Sepal color.*—374.
- *Number of anthers.*—32.
- *Anther color.*—498.
- *Number of stamens.*—32.
- *Stamen length.*—13/16".
- *Stamen color.*—413.
- *Pistil length.*—¾".
- *Pistil color.*—102.
- *Pollen.*—Present, self-fertilizing.
- *Flower and petal color.*—203.
- *Flowers per cluster.*—Usually two (2).
- *Petals per cluster.*—Five (5).
- *Fragrance.*—Very slight.

Fruit.
- *Maturity when described.*—Firm ripe.
- *Date of first picking.*—Aug. 5, 2001.
- *Date of last picking.*—Aug. 15, 2001.
- *Size.*—Large — average diameter 2¾".
- *Form.*—Spherical.
- *Suture.*—Not pronounced — stays very firm.
- *Weight.*—Average 7.3 oz.

Skin:
- *Thickness.*—Medium.
- *Texture.*—Medium.
- *Tendency to crack.*—None.
- *Down.*—Light.
- *Color.*—White-yellow ground color (100) — nearly overspread (60% to 80%) with red (214 to 215).

Flesh:
- *Texture.*—Extremely firm, non-melting, free of fiber.
- *Ripens.*—Evenly.
- *Flavor.*—Good.
- *Aroma.*—Pleasant.
- *Eating quality.*—Good.
- *Color.*—Light yellow ( 100) — pit cavity bright red (214).

Stone:
- *Type.*—Very freestone.
- *Size.*—Approximately 1½" long — approximately 1" wide — approximately ¾" thick.
- *Form.*—Ovid.
- *Base.*—Straight.
- *Apex.*—Very sharply pointed.
- *Sides.*—Uneven.
- *Surface.*—Irregularly furrowed.
- *Color.*—Brown (222).
- *Tendency to crack.*—Slight.
- *Kernel.*—⅝" long, 7/16"wide, 1/32" thick.

Use: Desert.

Shipping quality: Excellent

Keeping quality: Excellent.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree, substantially as herein illustrated and described.

* * * * *

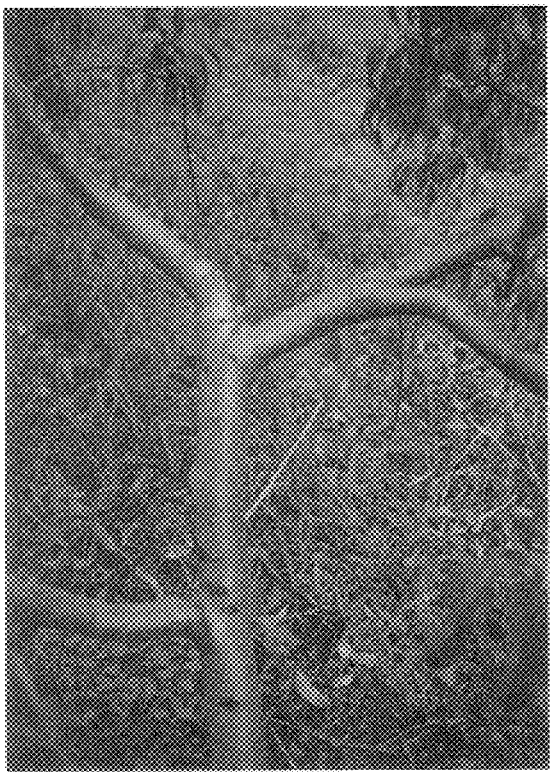
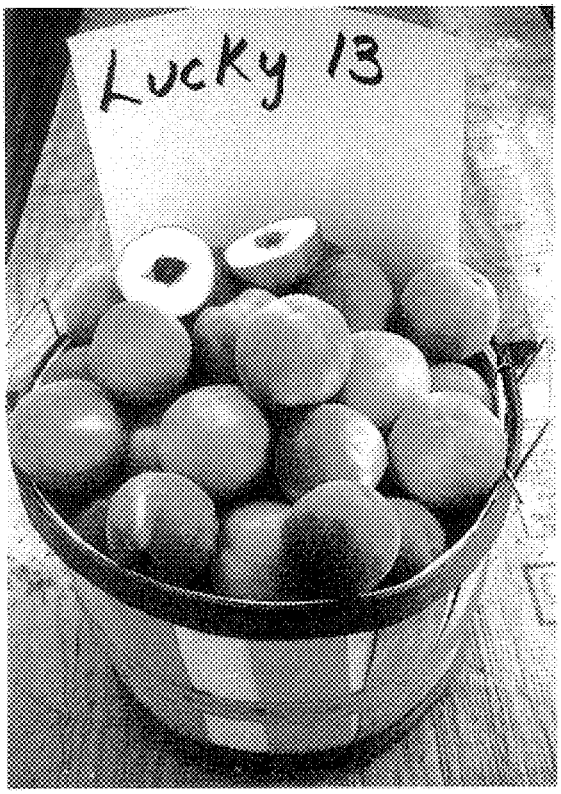
Lucky 13

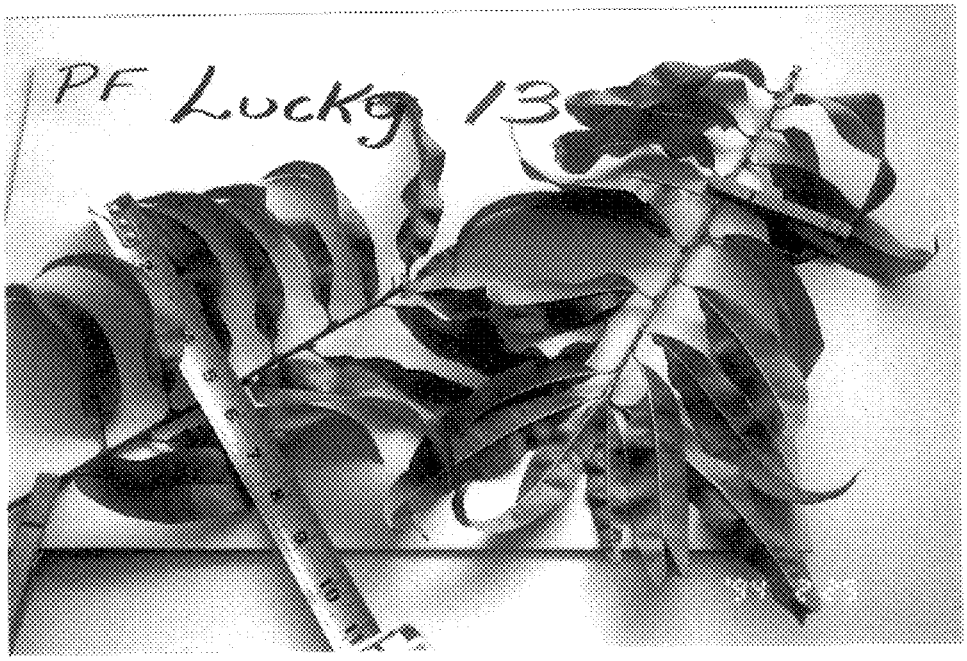
PF Lucky 13